(12) United States Patent
Carol

(10) Patent No.: US 9,974,983 B2
(45) Date of Patent: May 22, 2018

(54) TISSUE STABILIZATION FOR THERAPEUTIC ULTRASOUND

(71) Applicant: SonaCare Medical LLC, Charlotte, NC (US)

(72) Inventor: Mark Carol, Charlotte, NC (US)

(73) Assignee: SONACARE MEDICAL, LLC, Charlotte, NC (US)

( * ) Notice: Subject to any disclaimer, the term of this patent is extended or adjusted under 35 U.S.C. 154(b) by 174 days.

(21) Appl. No.: 14/938,995

(22) Filed: Nov. 12, 2015

(65) Prior Publication Data

US 2017/0136266 A1    May 18, 2017

(51) Int. Cl.
| | |
|---|---|
| A61N 7/02 | (2006.01) |
| A61M 25/10 | (2013.01) |
| A61B 17/22 | (2006.01) |
| A61N 7/00 | (2006.01) |
| A61B 17/225 | (2006.01) |
| A61B 18/00 | (2006.01) |

(52) U.S. Cl.
CPC .......... A61N 7/022 (2013.01); A61M 25/1018 (2013.01); A61B 2017/22015 (2013.01); A61B 2017/2253 (2013.01); A61B 2017/22054 (2013.01); A61B 2017/22062 (2013.01); A61B 2018/00023 (2013.01); A61M 2025/1013 (2013.01); A61N 2007/0043 (2013.01); A61N 2007/0052 (2013.01)

(58) Field of Classification Search
CPC .......... A61B 2017/22015; A61B 2017/22054; A61B 2017/22062; A61B 2017/2253; A61B 2018/00023; A61M 2025/1013; A61M 25/1018; A61N 2007/0043; A61N 2007/0052; A61N 7/022

See application file for complete search history.

(56) References Cited

U.S. PATENT DOCUMENTS

| | | | |
|---|---|---|---|
| 5,601,526 | A | 2/1997 | Chapelon et al. |
| 6,685,640 | B1 | 2/2004 | Fry et al. |
| 7,559,905 | B2 | 7/2009 | Kagosaki et al. |
| 7,662,114 | B2 | 2/2010 | Seip et al. |

(Continued)

FOREIGN PATENT DOCUMENTS

| | | |
|---|---|---|
| CA | 2699408 A1 | 9/2008 |
| CA | 2706563 A1 | 6/2009 |

(Continued)

OTHER PUBLICATIONS

International Patent Application No. PCT/US17/13853 filed Jan. 18, 2017. SonaCare Medical LLC.

(Continued)

Primary Examiner — Ruth S Smith
(74) Attorney, Agent, or Firm — Mark T. Vogelbacker; Eckert Seamans Cherin & Mellott, LLC

(57) ABSTRACT

A device including a focused ultrasound probe, a first balloon, and a second balloon. The first balloon can be located at least partially inside the second balloon. The inner balloon can be configured to act as a fluid interface, a mechanism for cooling, and a mechanism for changing tissue depth of a focal point of the probe. The second balloon can be filed with a thermosensitive hydrogel configured to turn from a fluid at room temperature to a gel at physiologic temperatures. The first and second balloons can be configured to create a fluid interface between the probe and targeted tissue of a patient.

10 Claims, 4 Drawing Sheets

(56) References Cited

U.S. PATENT DOCUMENTS

| | | |
|---|---|---|
| 7,722,839 B2 | 5/2010 | Kuzyk |
| 8,038,631 B1 | 10/2011 | Sanghvi et al. |
| 8,162,858 B2 | 4/2012 | Manna |
| 8,235,902 B2 | 8/2012 | Chen et al. |
| 9,095,695 B2 | 8/2015 | Fedewa et al. |
| 9,409,041 B2 | 8/2016 | Fedewa et al. |
| 9,457,202 B2 | 10/2016 | Sanghvi et al. |
| 2002/0068885 A1 | 6/2002 | Harhen et al. |
| 2002/0087081 A1 | 7/2002 | Serrano |
| 2005/0055012 A1 | 3/2005 | Trerotola |
| 2006/0137697 A1 | 6/2006 | Murphy et al. |
| 2007/0066897 A1 | 3/2007 | Sekins et al. |
| 2007/0224169 A1 | 9/2007 | Sliwa et al. |
| 2010/0152590 A1 | 6/2010 | Moore |
| 2010/0240002 A1 | 9/2010 | Halevy-Politch et al. |
| 2011/0098609 A1 | 4/2011 | Hall et al. |
| 2011/0098684 A1 | 4/2011 | Trubiano |
| 2013/0096552 A1 | 4/2013 | Brace et al. |
| 2013/0165823 A1 | 6/2013 | Ishibashi et al. |
| 2013/0197555 A1 | 8/2013 | Schaer |
| 2013/0248446 A1 | 9/2013 | Frugier |
| 2014/0243677 A1 | 8/2014 | Johnson et al. |
| 2014/0277035 A1 | 9/2014 | Strait et al. |
| 2014/0330124 A1 | 11/2014 | Carol |
| 2014/0330175 A1 | 11/2014 | Carol |
| 2015/0066007 A1 | 3/2015 | Srivastava |
| 2015/0321027 A1 | 11/2015 | Fedewa et al. |
| 2016/0235484 A1 | 8/2016 | Carol |
| 2016/0236013 A1 | 8/2016 | Carol et al. |
| 2016/0332005 A1 | 11/2016 | Fedewa et al. |

FOREIGN PATENT DOCUMENTS

| | | |
|---|---|---|
| CA | 2662997 C | 1/2016 |
| CN | 106061401 A | 10/2016 |
| EP | 2207596 B1 | 5/2013 |
| EP | 1755458 B1 | 2/2015 |
| EP | 2069018 B1 | 7/2016 |
| EP | 3054858 A1 | 8/2016 |
| EP | 3055027 A1 | 8/2016 |
| EP | 3108934 A1 | 12/2016 |
| JP | 5064386 B2 | 10/2012 |
| JP | 5462167 B2 | 4/2014 |
| JP | 5615548 B2 | 10/2014 |
| JP | 2016533784 A | 11/2014 |
| JP | 6046094 B2 | 12/2016 |
| JP | 2016538014 A | 12/2016 |
| KR | 20160068922 A | 6/2016 |
| WO | 2015054592 A1 | 4/2015 |
| WO | 2015054605 A1 | 4/2015 |

OTHER PUBLICATIONS

U.S. Appl. No. 62/398,752, filed Sep. 23, 2016. Seip et al.
U.S. Appl. No. 62/433,989, filed Dec. 14, 2016. Seip et al.
U.S. Appl. No. 62/331,161, filed May 3, 2016. Carol et al.
U.S. Appl. No. 15/408,617, filed Jan. 18, 2017. Carol et al.
International Patent Application No. PCT/US16/59844 filed Nov. 1, 2016. SonaCare Medical LLC.
International Search Report and Written Opinion, dated Feb. 6, 2017, in corresponding International Patent Application No. PCT/US2016/059844.

TISSUE STABILIZATION FOR THERAPEUTIC ULTRASOUND

SUMMARY

Focused ultrasound can be used to deliver energy concentrated in targeted tissue on or inside a patient, while minimizing the amount of energy deposited in any other tissue between the probe delivering the energy and the targeted tissue. In order to deliver correctly the desired amount of energy to the targeted or localized tissue, the probe must be positioned and stabilized correctly geometrically relative to the targeted or desired tissue and held in that position during the course of treatment. However, there are operating principles that make this difficult to achieve.

Satisfactory delivery of therapeutic focused ultrasound benefits from a lack of air and bone, as well as other obstructions along the path, between the transducer and the target tissue. This necessitates usually the creation of a liquid coupling interface between the probe and tissue, with the liquid being contained within a membrane or balloon. The volume of liquid can be increased or decreased to adjust the position of the probe relative to the tissue—increasing the volume pushes the probe further from the surface tissue and brings the focal point of the probe closer to the surface, while decreasing it brings the probe closer to the surface tissue thereby pushing the focal point of the probe deeper into the tissue. It is desirable for the liquid to exist in a fluid state so it can be circulated and used to remove excess heat from the surface of the probe, thereby extending the life of the crystal(s) used to generate the focused ultrasound and ensuring proper performance. However, surrounding the probe with a "fluid filed sac" or fluid interface can introduce the potential for sac or interface to move relative to the target tissue and, therefore, the probe to move relative to the target tissue.

Therefore, it would be desirable to produce a means that will allow a fluid interface between the probe and the tissue to be created without destabilizing the interface between the probe and the tissue.

In one embodiment, the present disclosure includes a device and/or method configured to create a fluid interface between a focused ultrasound probe and tissue containing targeted tissue, while also stabilizing the geometric position between the probe and the tissue. A double balloon can be provided, with one distensible balloon located inside the other distensible balloon, the inner balloon being filled with water, where the inner balloon acts as a fluid interface and a mechanism for cooling and a mechanism for changing the tissue depth of the focal point, the outer balloon being filled with a thermosensitive hydrogel that turns from a fluid at room temperature to a gel at physiologic temperatures, thereby allowing the gel to act to immobilize the inner balloon relative to the outer balloon and the outer balloon relative to the surrounding tissue.

In a further embodiment, the present disclosure includes a method for treating tissue with focused ultrasound, the method can include: inserting a dual balloon port into a natural or man-made orifice in a patient; inserting a probe capable of delivering therapeutic ultrasound into a first, inner balloon; filling the inner balloon with a free flowing liquid; positioning the balloon complex in the correct position for treating the targeted tissue; filling a second, outer balloon with enough thermosensitive hydrogel to engulf or achieve significant contact with the region of tissue containing the targeted tissue; adding fluid to the inner balloon to create the proper delivery depth if required; allowing or forcing the hydrogel to undergo a sol-gel transition; delivering the ultrasound therapy; allowing or forcing the hydrogel to undergo a gel-sol transition; removing the hydrogel from the outer balloon; removing the free flowing fluid from the inner balloon; removing the probe from the inner balloon; removing the balloon port from the tissue; whereby an ultrasound treatment can be delivered with a stable geometry between the ultrasound probe and the targeted tissue and with correct and safe functioning of the ultrasound probe.

As is to be appreciated by one skilled in the art, one or more aspects of the foregoing disclosed systems and methods may be combined or even omitted, if desirable.

DRAWINGS

The foregoing summary, as well as the following detailed description of the invention, will be better understood when read in conjunction with the appended drawings. For the purpose of illustrating the invention, there are shown in the drawings various illustrative embodiments. It should be understood, however, that the invention is not limited to the precise arrangements and instrumentalities shown. In the drawings.

DETAILED DESCRIPTION

Figure 1:
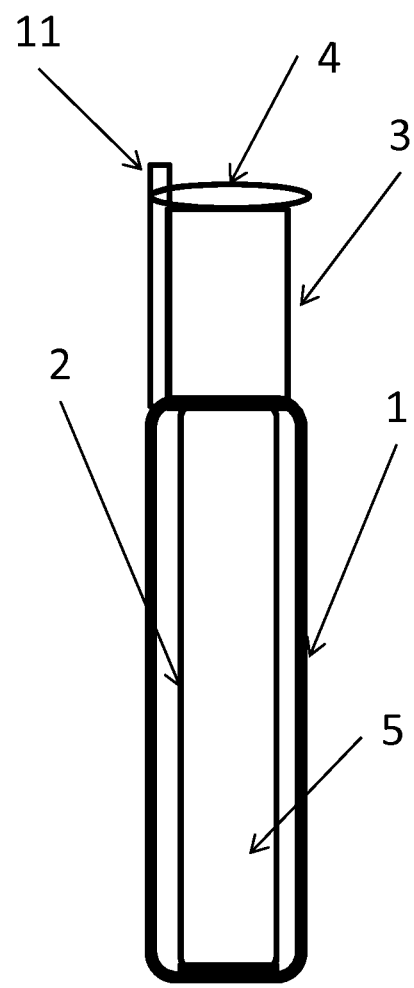
FIG. 1 is a schematic representation of a system according to an embodiment of the present invention.
Figure 2:
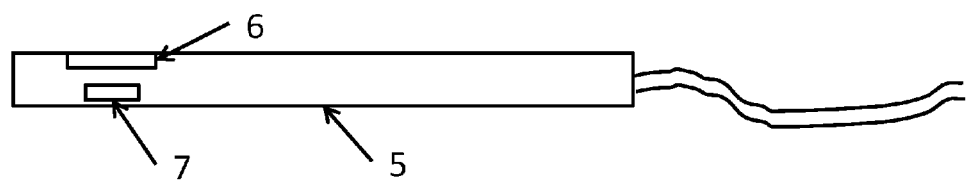
FIG. 2 is a schematic representation of at least a portion of a probe according to an embodiment of the present invention.
Figure 3:
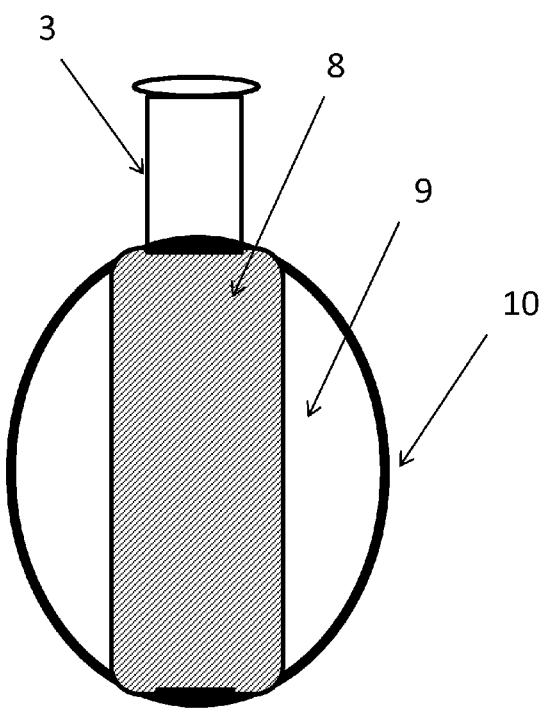
FIG. 3 is a schematic representation of a balloon complex of the system in a secondary or expanded state.

Various embodiments of the present disclosure are described hereinafter with reference to the figures. It should be noted that the figures are not drawn to scale and elements of similar structures or functions are represented by like reference numerals throughout the figures. It should also be noted that the figures are not intended to facilitate the description of specific embodiments of the invention. The figures are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention. It will be appreciated that while various embodiments of the invention are described in connection with focused ultrasound treatment of tumors, the claimed invention has application in other industries and to targets other than cancers. Unless specifically set forth herein, the terms "a," "an" and "the" are not limited to one element, but instead should be read as "at least one."

Referring to FIGS. 1-5, the present disclosure relates to a system for performing a surgical procedure. In one embodiment, the system can include at least one transducer positioned in or on a probe 5 (as understood by those skilled in the art) used to deliver thermal energy to a designated treatment volume 17 through one or more therapy crystals 6. The transducer may be configured to include one or more imaging crystals 7 used to generate one or more images of the designated treatment volume and surrounding tissue. The images can be used to position correctly the volume of tissue targeted for the delivery of thermal energy. A user input interface can be provided to define the region, volume, and/or location of tissue designated to receive the thermal energy. The transducer can include one or more individual therapy crystals, each with a fixed focal point acting independently, or it can include one or more groupings of multiple crystals, which together form an annular, linear, 2-D, or other form of array where the focal point of each group of crystals can be moved electronically. The probe 5 can include one or more motors integral to its housing used to translate and/or rotate the transducer relative to the probe housing or can use one or more motors external to the probe 5 to translate and/or rotate the transducer relative to the probe housing.

Referring to FIG. 1, the system can include a balloon complex having a balloon-within-a-balloon design. More particularly, the system can include a first, inner balloon 2 wholly contained within a second, outer balloon 1, except for at their necks 3 where each balloon 2, 1 can have its own ingress and egress port(s). The inner balloon 2 can be designed to be symmetrically expandable 8 (see FIG. 3) or can be constructed so that it expands at different rates, and to different degrees, in different directions. Regardless, in at least one embodiment, the inner balloon 2 will remain taut when expanded (see FIG. 3) and would not conform to a contacting surface. The outer balloon 1 can be designed to expand in a free-form manner 9 (see FIG. 3) depending, for example, on the tissue 18 against which it comes in contact, allowing it to adopt or conform (at least in part) to the shape of that tissue 18. Alternatively, the outer balloon 1 can be designed to be symmetrically expandable (similar to one embodiment of the inner balloon 2 shown in FIG. 3), or can be constructed so that it expands at different rates, and to different degrees, in different directions, etc.

In one embodiment, a single port (for both ingress and egress of fluid) can be provided for each balloon 2, 1 at or near the neck 3 thereof. Each port can be either self-sealing or can be controlled with a valve, luer lock, or similar mechanism. Alternatively, an egress port and a separate ingress port can be provided for each balloon 2, 1 at or near the neck thereof. In such an embodiment, the egress port can be spaced-apart from the ingress port. For the outer balloon 1, the port(s) can be used to remove air from the outer balloon 1 and to inject and remove a fluid, such as a hydrogel. For the inner balloon 2, the port(s) can be used to remove air from the inner balloon 2 and pass the ultrasound probe at least partially into the inner balloon 2. Water or another fluid can be injected into the inner balloon 2 through the port(s) or it can be instilled into the inner balloon 2 through an opening in the ultrasound probe 5.

Figure 4:
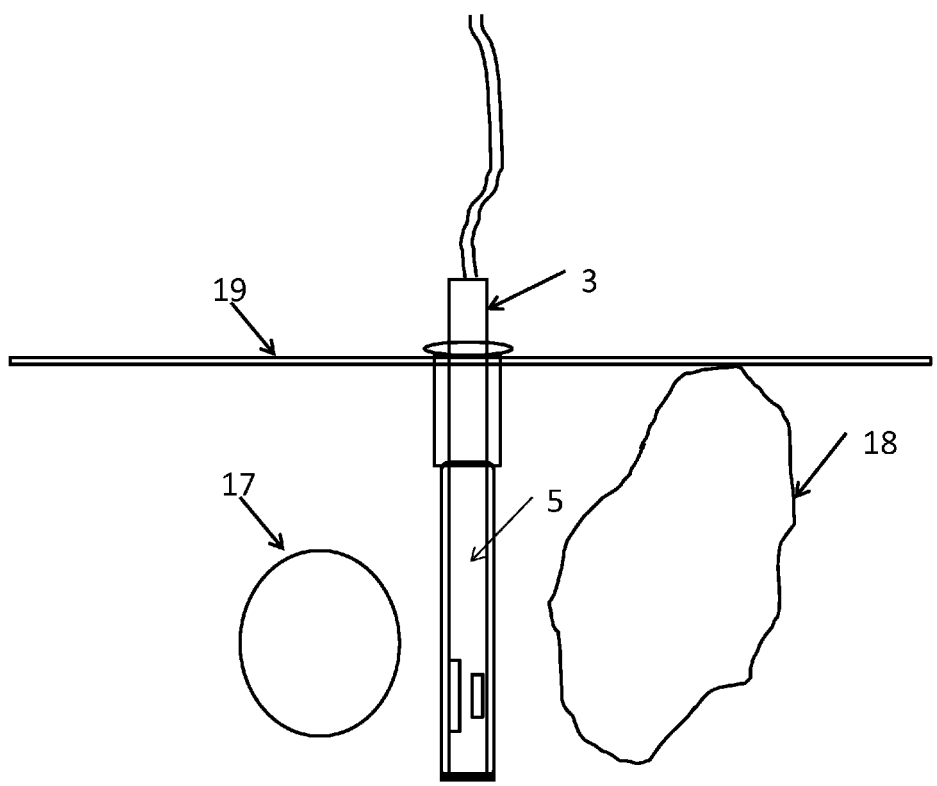
FIG. 4 is a schematic representation of a probe inserted into a cavity of a patient, wherein the balloon complex is in at least a partially collapsed or constricted state.
Figure 5:
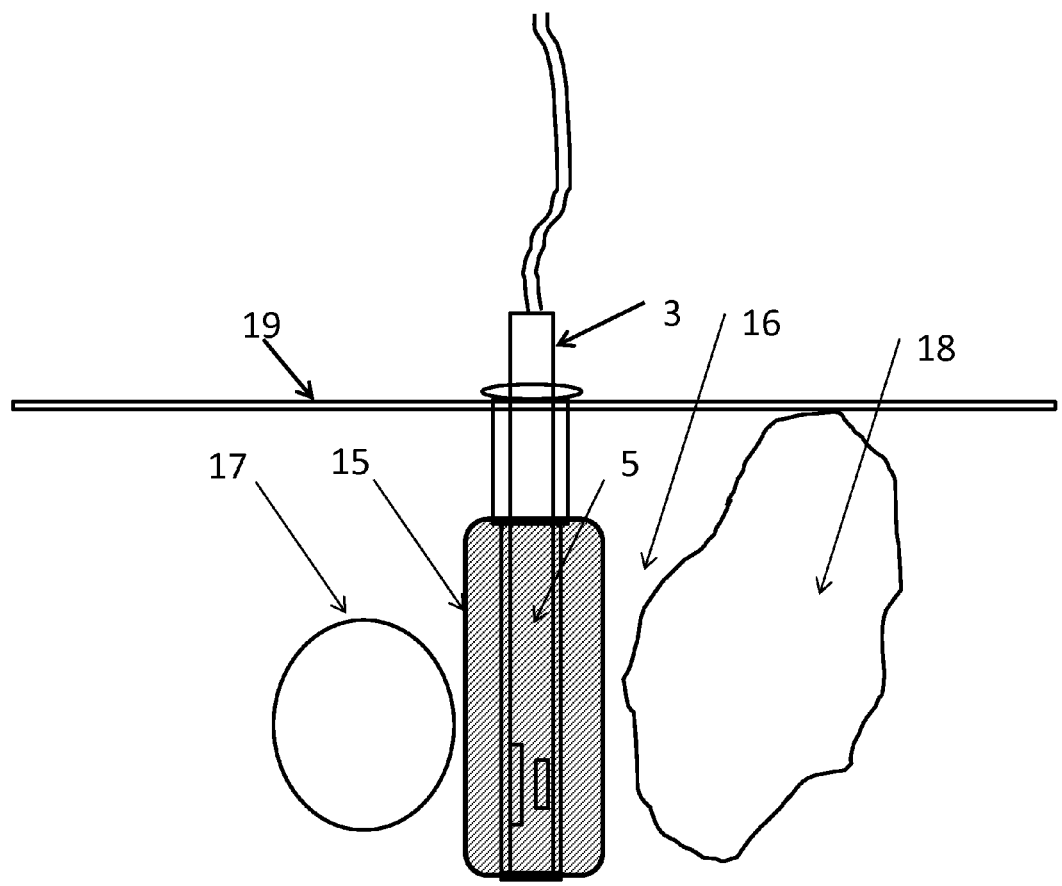
FIG. 5 is a schematic representation of a probe inserted into a cavity of a patient, wherein the balloon complex is in at least a partially expanded state.

The neck 3 common to the two balloons 2, 1 can be configured with a flared outer surface ring or collar 4 (see FIG. 1) that prevents the balloon complex from being pushed in its entirety into the artificial or natural cavity in a patient 19 (see FIGS. 4 and 5). The ingress and egress port(s) can be incorporated into this flared surface 4 or can exit either or both of the balloons 2, 1 via separate tubing 11.

Temperature sensitive hydrogels undergo a solution (sol) to gel (gel) transition at a predetermined temperature. In the sol state, the hydrogel is free flowing. In the gel state, the gel sets up as a solid that does not flow and retains the shape of the vessel or container 10 in which it is contained. Such a material can be injected into the outer balloon 1 at room temperatures or at a cooled temperature as a free flowing liquid. Once it is inside the outer balloon 1, which can be at least partially or completely positioned inside a natural or artificial cavity in a patient 19, the hydrogel is exposed to physiologic temperatures (e.g., 96 to 104 degrees Fahrenheit). By using a hydrogel, whose sol-gel transition occurs at physiologic temperatures, the hydrogel can be used to fix the shape of the outer balloon 1 that is created by its contact with surrounding tissue 18. The time required for this to occur, and the time available to allow the outer balloon 1 to conform to the surrounding tissues 18, can be controlled by infusing water at less than physiologic temperatures or the sol-gel transition temperature, into the artificial or natural cavity of the patient 19, thereby bathing the outer balloon 1 in the water and reducing the temperature to which it is exposed for some period of time. This approach—bathing the surrounding cavity in a fluid that is below the sol-gel transition temperature, also can be used to cause a gel-sol transition so that the hydrogel can be removed from the outer balloon 1 The gel-sol transition can be aided by cycling cold water through the inner balloon 2, which will cool the hydrogel from the "inside out."

An alternative approach is to use a hydrogel that has a sol-gel transition temperature that is greater than physiologic temperatures. Such a temperature can be achieved in the hydrogel by infusing water that is above physiologic temperature into the cavity surrounding the balloon or into the inner balloon 2. In this case, the gel-sol transition would occur naturally as the bathing fluid either cools down or is removed, and can be aided by circulating cold water through the inner balloon 2.

A higher than physiologic temperature also can be achieved in the hydrogel by turning on the ultrasound probe 5 and using its energy to warm the hydrogel as the probe 5 passes through the hydrogel. Since some portion of the ultrasound energy will be absorbed by the hydrogel during the treatment, this approach insures that the hydrogel will remain in a gel state for the entire duration of the treatment.

The hydrogel can be impregnated with various biologic substances selected to act in concert with the ultrasound, distinct from the ultrasound, or to be activated by the ultrasound. The material used for the membrane of the outer balloon 1 can be porous, thereby allowing substances suspended in the hydrogel to leach out of the hydrogel across the membrane and into the tissue against which the membrane is juxtaposed. The membrane used for the outer balloon 1 also can be nonporous. The molecular configuration of the hydrogel also can be used to modify the focal point of the therapeutic ultrasound probe. By using a gel with a diffraction index different from water, the gel can act as a lens that will change the focus of the ultrasound energy.

Typically, fluid that has the density of water is transparent to ultrasound energy. Thus, depending on the actual tissue path length the beam travels through on its way to the geometric focal point of the crystal being used, the amount of energy attenuation by the tissue will vary, requiring that the power applied to the crystal may have to be varied in order to ensure that a constant amount of heat is delivered to the tissue at the focal point. If hydrogel is used that has a density in its gel state that is equivalent to that of tissue, the effective tissue path from the crystal to the focal point will become constant and independent of the actual tissue path length through which the beam travels, meaning that a constant power setting can be used to deliver the treatment, reducing the complexity of the physician interaction with the device.

Referring to FIGS. 4 and 5, in use, the dual balloon, with air having been evacuated from both balloons 2, 1 and their associated valves or ports closed in order to make the over profile as small as possible, can be inserted into a natural or man-made orifice in a patient 19 with the collar 4 sitting on the orifice surface. A stylet can be inserted into the inner balloon 2 through the port to aid in the insertion of the balloons 2, 1 or the ultrasound probe 5 can be inserted in the inner balloon 2 prior to balloon insertion to stiffen the balloons. Once in place, and if the probe 5 was not used to insert the balloon(s), the probe 5 can be passed through the valve or port into the inner balloon 2. Water can be circulated through the probe 5, thereby filling the inner balloon 2 with fluid 15 (see FIG. 5). The amount of fluid can be controlled by mechanisms internal or external to the probe control system. This water can be chilled in order to reduce heat buildup at the surface of the ultrasound crystal within the transducer or to produce a gel-sol transition at the end of the treatment.

The balloon and probe 5 can be adjusted to be in the correct position for treating the targeted tissue based on the use of either on-board probe imaging capability or other means. The outer balloon 1 can then be filled with enough of the thermosensitive hydrogel to cause the outer balloon 1 to expand and engulf, surround or achieve significant contact with the region of tissue containing the targeted tissue 17. While the hydrogel is still in a free flowing state, fluid can be added to the inner balloon 2 to create the proper delivery depth, if required. Increasing the volume or size of at least the inner balloon 2 pushes the probe 5 further from the surface of the tissue being treated, thereby bringing the focal point of the probe 5 closer to the surface, while decreasing the volume or size of at least the inner balloon 2 brings the probe 5 closer to the surface tissue, thereby pushing the focal point of the probe 5 deeper into the tissue. Tissue depth can also be adjusted by controlling the amount of solution injected into the outer balloon.

The hydrogel can then be allowed, via physiologic means, or forced, by turning on the ultrasound probe 5 or instilling fluid above physiologic temperatures into the cavity, to undergo a sol-gel transition 16 (see FIG. 5). This causes the shape of the outer balloon 1 to become fixed, thereby immobilizing the surrounding tissue 18 relative to the outer balloon 2 and the outer balloon 2 relative to the inner balloon 1. The ultrasound treatment can then be delivered, taking advantage of the heat transferred to the hydrogel to maintain it in the gel state.

Once the ultrasound delivery is completed, the hydrogel can be forced to undergo a gel-sol transition by infusing cold water into the treatment cavity, by infusing cold water into the inner balloon 2, or by letting the gel cool to physiologic temperatures if a hydrogel was used that as a sol-gel transition temperature greater than body temperature. As the gel-sol transition occurs, the hydrogel can be removed from the outer balloon 1 by applying suction to the egress port. Once all or substantially all of the hydrogel is removed from the outer balloon 1, the probe 5 can be removed from the inner balloon 2, the water removed from the inner balloon 2, suction applied to both balloons 2, 1 to reduce their profile as much as possible if needed, and the entire balloon complex removed from the patient. It is understood by those skilled in the art that one or more of the above-described steps can be accomplished in an alternative or different order.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for treating tissue with focused ultrasound, the method comprising:
   inserting at least a portion of an ultrasound probe into an inner balloon of a balloon complex, the balloon complex including the inner balloon at least partially surrounded by an outer balloon;
   inserting the balloon complex in an orifice of a patient;
   injecting thermosensitive hydrogel into the outer balloon to cause the outer balloon to engulf or contact a region of tissue of the patient containing targeted tissue;
   injecting liquid into the inner balloon;
   allowing or causing the hydrogel to undergo a sol-gel transition;
   delivering focused ultrasound, via the ultrasound probe, to the targeted tissue; and
   removing the balloon complex from the orifice.

2. The method according to claim 1, wherein prior to removing the balloon complex the method comprises:
   allowing or causing the hydrogel to undergo a gel-sol transition;
   removing the hydrogel from the outer balloon;
   removing the liquid from the inner balloon; and
   removing the probe from the inner balloon.

3. The method according to claim 2, further comprising:
   infusing water into the orifice to cause the hydrogel to undergo the gel-sol transition.

4. The method according to claim 2, further comprising:
   removing the hydrogel from the outer balloon by applying suction to an egress port of the balloon complex.

5. The method according to claim 1, further comprising, evacuating air from the inner and outer balloons prior to positioning the balloon complex in the orifice.

6. The method according to claim 1, further comprising:
   closing a port of the balloon complex prior to positioning the balloon complex in the orifice.

7. The method according to claim 1, further comprising:
   prior to inserting the balloon complex in the orifice, inserting a stylet into the inner balloon.

8. The method according to claim 1, further comprising:
   infusing water at a temperature less than the sol-gel transition temperature into the orifice of the patient.

9. A method for treating tissue with focused ultrasound, the method comprising the steps of:
   a) evacuating air from a balloon complex, the balloon complex including an inner balloon at least partially surrounded by an outer balloon;
   b) inserting both a probe and a stylet into the inner balloon;
   c) closing a port of the balloon complex;
   d) inserting the balloon complex in an orifice of a patient;
   e) injecting thermosensitive hydrogel into the outer balloon to cause the outer balloon to engulf or contact a region of tissue of the patient containing targeted tissue;
   f) injecting liquid into the inner balloon;
   g) allowing or causing the hydrogel to undergo a sol-gel transition which causes the shape of the outer balloon to be at least generally fixed thereby immobilizing surrounding tissue of the patient relative to the outer balloon;
   h) delivering focused ultrasound, via the probe, to the targeted tissue;
   i) allowing or causing the hydrogel to undergo a gel-sol transition by infusing water into the orifice;

j) removing the hydrogel from the outer balloon by applying suction to an egress port of the balloon complex;
k) removing the liquid from the inner balloon;
l) removing the probe from the inner balloon and;
m) removing the balloon complex from the orifice.

10. The method according to claim 9, wherein the step of infusing water comprises infusing water at a temperature less than the sol-gel transition temperature.

* * * * *